United States Patent
Katrukha et al.

(10) Patent No.: US 7,285,418 B2
(45) Date of Patent: Oct. 23, 2007

(54) METHOD AND KIT FOR THE DIAGNOSIS OF TROPONIN I

(75) Inventors: Alex G. Katrukha, Moscow (RU); Sergei Severin, Moscow (RU); Anastasia Bersenikova, Moscow (RU); Tatiana Esakova, Moscow (RU); Kim Pettersson, Turku (FI)

(73) Assignee: Hytest Ltd., Turku (FI)

( * ) Notice: Subject to any disclaimer, the term of this patent is extended or adjusted under 35 U.S.C. 154(b) by 631 days.

(21) Appl. No.: 10/187,310

(22) Filed: Jul. 1, 2002

(65) Prior Publication Data

US 2003/0040024 A1  Feb. 27, 2003

Related U.S. Application Data

(63) Continuation of application No. 09/102,328, filed on Jun. 22, 1998, now abandoned, which is a continuation-in-part of application No. PCT/FI97/00399, filed on Jun. 23, 1997, which is a continuation-in-part of application No. 08/670,013, filed on Jun. 25, 1996, now abandoned.

(51) Int. Cl.
   *G01N 31/00* (2006.01)
(52) U.S. Cl. ............... 436/16; 435/7.1; 435/7.94; 436/8; 436/15; 436/16; 436/17; 436/18; 436/164; 436/166; 436/172; 436/176; 436/177; 436/517; 530/380
(58) Field of Classification Search ............ 435/2, 435/6, 7.1, 7.2, 7.5, 7.92, 7.94; 436/503, 436/826, 517, 544, 546, 15–18, 66, 199, 436/176, 177, 523, 8, 164, 166, 172; 530/350, 530/387.9; 422/61
See application file for complete search history.

(56) References Cited

U.S. PATENT DOCUMENTS 4,950,612 A   8/1990   Khanna et al. ............. 436/505

(Continued)

FOREIGN PATENT DOCUMENTS

EP   0 743 522 A1   11/1996

(Continued)

OTHER PUBLICATIONS

Hunt et al., "Release of creatine kinase-MB and cardiac specific troponin-I following percutaneous transluminal coronary angioplasty," *European Heart Journal*, vol. 12, pp. 690-694 (1991).

(Continued)

*Primary Examiner*—Gailene R. Gabel
(74) *Attorney, Agent, or Firm*—Marshall Gerstein & Borun LLP

(57) ABSTRACT

The invention provides a method for assaying for troponin I in a sample such as serum, the method comprising a determination of the troponin I concentration in a sample using a standard preparation that comprises a complete native troponin complex. One exemplary assay for troponin I concentration according to the invention is an immunoassay. Further contemplated in the method is a step comprising contacting the sample with a $Ca^{2+}$-binding agent. Another aspect of the invention is the standard preparation comprising a complete native troponin complex. Yet another aspect of the invention is a kit for use in the assay method comprising the standard preparation, a detectable label, and a troponin I binding partner, such as an anti-troponin I antibody. All aspects of the invention are usefully practiced using human materials, such as a human troponin complex, and/or human sources for samples.

12 Claims, 9 Drawing Sheets

U.S. PATENT DOCUMENTS

Figure 1:
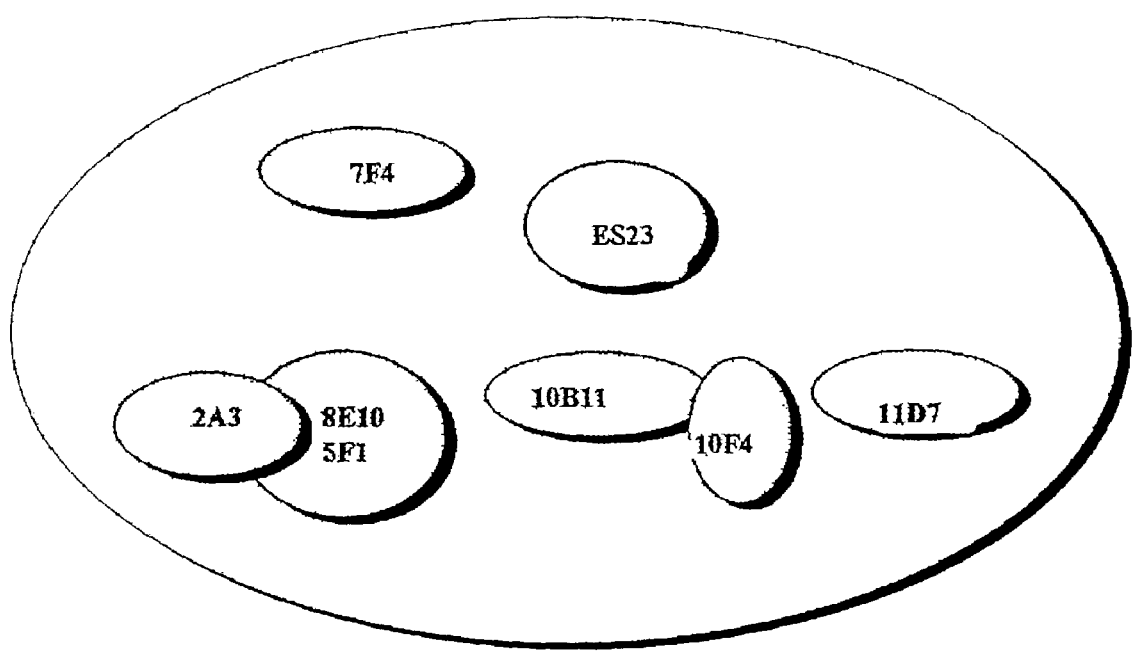

| | | | | |
|---|---|---|---|---|
| 6,174,686 | B1* | 1/2001 | Buechler et al. | 435/7.1 |
| 2004/0033529 | A1* | 2/2004 | Riochet | 435/7.2 |

FOREIGN PATENT DOCUMENTS

| | | |
|---|---|---|
| GB | 2275774 | 9/1994 |

OTHER PUBLICATIONS

Bodor et al., "Development of Monoclonal Antibodies for an Assay of Cardiac Troponin-I and Preliminary Results in Suspected Cases of Myocardial Infarction," *Clinical Chemistry*, vol. 38, No. 11, pp. 2203-2214 (1992).

Adams et al., "Cardiac Troponin I—A Marker With High Specificity for Cardiac Injury," *Circulation*, vol. 88, No. 1, pp. 101-106 (Jul. 1993).

Adams et al., "Comparable Detection of Acute Myocardial Infarction by Creatine Kinase MB Isoenzyme and Cardiac Troponin I," *Clinical Chemistry*, vol. 40, No. 7, pp. 1291-1295 (1994).

Mair et al., "Equivalent Early Sensitivities of Myoglobin, Creatine Kinase MB Mass, Creatine Kinase Isoform Ratios, and Cardiac Troponins I and T for Acute Myocardial Infarction," *Clinical Chemistry*, vol. 41, No. 9, pp. 1266-1272 (1995).

Katrukha et al., "A New Method of Human Cardiac Troponin I and Troponin T Purification," *Biochemistry and Molecular Biology International*, vol. 36, No. 1, pp. 195-202 (May 1995).

Chapelle et al., "Early Assessment of Coronary Reperfusion After Fibrinolysis by Measuring cTnI, CK-MB and Myoglobin in Serum," *Ischaemic Myocardial Damage-Early Detection: Biochemical Markers, The European Heart House* (Feb. 8-10, 1996).

Fournis et al., "Opus Troponin I as a Marker of Myocardial Damage," *Ischaemic Myocardial Damage-Early Detection: Biochemical Markers*, The European Heart House (Feb. 8-10, 1996).

Bertinchant et al., "Serum cardiac troponin I in unstable angina: an accurate prognostic marker for subsequent cardiac events," *Ischaemic Myocardial Damage-Early Detection: Biochemical Markers, The European Heart House* (Feb. 8-10, 1996).

Filice, et al., "Compared Usefulness of CK, Myoglobin and Cardiac Troponin I in Patients Presenting in the Emergency Department with Chest Pain," *Ischaemic Myocardial Damage-Early Detection: Biochemical Markers, The European Heart House* (Feb. 8-10, 1996).

Dolci et al., "Troponin-I in preoperative panel for kidney and pancreas transplant: a case report," *Ischaemic Myocardial Damage-Early Detection: Biochemical Markers, The European Heart House* (Feb. 8-10, 1996).

La Vecchia et al., "Troponin I is more sensitive than Creatine Kinase-MB mass in detecting periprocedural myocardial damage in coronary angioplasty: results from 57 consecutive patients," *Ischaemic Myocardial Damage-Early Detection: Biochemical Markers, The European Heart House* (Feb. 8-10, 1996).

Vernocchi et al., "Cardiac Troponin-I: A Specific Marker of Myocardial Necrosis," *Ischaemic Myocardial Damage-Early Detection: Biochemical Markers, The European Heart House* (Feb. 8-10, 1996).

Musso et al., "Cardiac Troponin-T and Cardiac Troponin-I in Unstable Angina: Incidence, Correlation, Release Kinetics and Prognostic Value," *Ischaemic Myocardial Damage-Early Detection: Biochemical Markers, The European Heart House* (Feb. 8-10, 1996).

Fiocchi et al. "Troponin I as a specific marker for cardiac damage after Heart Transplantation in Becker dystrophy," *Ischaemic Myocardial Damage-Early Detection: Biochemical Markers, The European Heart House* (Feb. 8-10, 1996).

Gilson et al., "Clinical Evaluation of Troponin I and Troponin T Measured by Different Assays," *Ischaemic Myocardial Damage-Early Detection: Biochemical Markers, The European Heart House* (Feb. 8-10, 1996).

Benamer et al., "Troponine I: Detection of Obstructive Coronary Artery Disease in Patients With Chest Pain at Rest," *Ischaemic Myocardial Damage-Early Detection: Biochemical Markers, The European Heart House* (Feb. 8-10, 1996).

Ottani et al., "Comparison Between Early Elevations of Troponin T and Troponin I in Patients with Unstable Angina," *Ischaemic Myocardial Damage-Early Detection: Biochemical Markers, The European Heart House* (Feb. 8-10, 1996).

Galvani et al., "Long-Term Prognostic Value of Elevated Cardiac Troponin I in Unstable Angina," *Ischaemic Myocardial Damage-Early Detection: Biochemical Markers, The European Heart House* (Feb. 8-10, 1996).

Zaninnotto et al., "Cardiac Troponin I in the Early Diagnosis of Acute Myocardial infarction Assayed with a New Fluoroenzymometric Method," *Ischaemic Myocardial Damage-Early Detection: Biochemical Markers, The European Heart House* (Feb. 8-10, 1996).

Trinquier et al., "Assessment of two highly specific immunoassays for cardiac troponin I in non-infarct patients with chronic renal failure or severe polytrauma," *Ischaemic Myocardial Damage-Early Detection: Biochemical Markers, The European Heart House* (Feb. 8-10, 1996).

Saintouil et al., "Automated Chemiluminescent Enzyme Immunoassay for the determination of human cardiac Troponin I," *Ischaemic Myocardial Damage-Early Detection: Biochemical Markers, The European Heart House* (Feb. 8-10, 1996).

Dehoux et al., "Cardiac Troponin I and Perioperative Myocardial Infarction After Cardiac Surgery," *Ischaemic Myocardial Damage-Early Detection: Biochemical Markers, The European Heart House* (Feb. 8-10, 1996).

Hafner et al., "Comparion of cardiac troponin I and troponin T in patients with unstable angina before and after percutaneous transluminal coronary angioplasty," *Ischaemic Myocardial Damage-Early Detection: Biochemical Markers, The European Heart House* (Feb. 8-10, 1996).

De La Farge et al., "Non Invasive Markers of Reperfusion in Acute Myocardial Infarction: CK-MB Mass, Myoglobin, Troponin Ic," *Ischaemic Myocardial Damage-Early Detection: Biochemical Markers, The European Heart House* (Feb. 8-10, 1996).

Bryan et al., "Does Normothermic Systemic Perfusion Compromise Cold Myocardial Protection During Coronary Artery Surgery?," *Ischaemic Myocardial Damage-Early Detection: Biochemical Markers, The European Heart House* (Feb. 8-10, 1996).

Collinson et al., "Cardiac troponin T, cardiac troponin I and CK-MB mass for routine investigation of patients admitted with suspected ischaemic cardiac disease," *Ischaemic Myocardial Damage—Early Detection: Biochemical Markers, The European Heart House* (Feb. 8-10, 1996).

Hossein-Nia et al., "Creatine Kinase MB Isoforms, and Troponins T and I: Sensitive Markers of Myocardial Damage in Pre-Clinical Studies," *Ischaemic Myocardial Damage-Early Detection: Biochemical Markers, The European Heart House* (Feb. 8-10, 1996).

Hossein-Nia et al., "Cardiac Troponin I in Patients Following Coronary Artery Bypass Grafting," *Ischaemic Myocardial Damage-Early Detection: Biochemical Markers, The European Heart House* (Feb. 8-10, 1996).

Li et al., "Greater Frequency of Increased Cardiac Troponin T than Increased Cardiac Troponin I in Patients with Chronic Renal Failure," *Clinical Chemistry*, vol. 42, No. 1 (1996).

Katrukha et al., "Time-Resolved Fluoroimmunoassay of Cardiac Troponin I," *Clinical Chemistry*, vol. 41, No. 6, p. S53, Abstract 090, (1995).

Syska et al., "A New Method of Preparation of Troponin I (Inhibitory Protein) Using Affinity *Chromatography*. Evidence for Three Different Forms of Troponin I in Striated Muscle," *FEBS Letters*, vol. 40, No. 2 pp. 253-257, (1974).

*Textbook of Clinical Chemistry*, Norbert W. Teitz, Ed., W.B. Saunders Company, Philadelphia, p. 1816, (1986).

Mair et al., "Use of Cardiac Troponin I to Diagnose Perioperative Myocardial Infarction in Coronary Artery Bypass Grafting" *Clinical Chemistry*, vol. 40, No. 11, pp. 2066-2070 (1994).

*Laboratory Medicine*, vol. 23, No. 5, May 1992, Hugo A. Katus et al., "Proteins of the Troponin Complex," pp. 311-317.

International Search Report of PCT/FI97/00399 dated Oct. 14, 1997, three pages.

* cited by examiner

METHOD AND KIT FOR THE DIAGNOSIS OF TROPONIN I

This is a continuation of U.S. patent application Ser. No. 09/102,328 filed Jun. 22, 1998, now abandoned, which is a continuation-in-part of International Patent Application No. PCT/FI97/00399, filed Jun. 23, 1997, which is a continuation-in-part of U.S. patent application Ser. No. 08/670,013 filed Jun. 25, 1996, now abandoned.

FIELD OF THE INVENTION

The object of the present invention is an improvement in a diagnostic immunoassay method for assaying human cardiac and skeletal troponins I (TnI) in a sample taken from the blood stream of a patient.

A further object of the invention is a kit for use in an improved diagnostic immunoassay method for assaying troponin I in a sample from the blood stream of a patient.

A still further object of the invention is an improved troponin I standard preparation for use in the method and kit according to the invention.

BACKGROUND OF THE INVENTION

Human cardiac troponin I (h.c. TnI) was recently suggested to be a specific and sensitive marker of myocardial cell death. It is released into the blood stream after myocardial damage, e.g. after acute myocardial infarction (AMI) (see e.g. Adams, J. E. et al., *Circulation* 1993; 88:101-106). Human skeletal troponin I (h.sk.TnI) has been suggested as a sensitive and specific marker of skeletal cell death.

TnI is the subunit of a troponin complex that plays an important role in the $Ca^{2+}$-dependent regulation of vertebrate skeletal and cardiac muscle contraction. The troponin complex is located on the thin filament of the contractile apparatus and through its association with two other thin filament proteins, actin and tropomyosin, inhibits the actomyosin interaction at submicromolar $Ca^{2+}$-concentrations, and stimulates interaction at micromolar and higher $Ca^{2+}$-concentrations. The troponin complex contains three subunits—troponin C (TnC), which is the $Ca^{2+}$-binding subunit; troponin I (TnI), which is the inhibitory subunit, and troponin T (TnT), which is the tropomyosin binding subunit. The interaction between the three subunits of the troponin complex is so strong that originally the purified troponin was thought to be a single protein.

The $Ca^{2+}$-dependent regulation is initiated by conformational changes in TnC and subsequent changes in the interaction of TnC with TnI. TnC is composed of two globular domains connected by a central helix. Each domain contains two metal-binding sites. Two sites in the N-terminal domain (sites I and II) bind $Ca^{2+}$ with low affinity, while sites in the C-terminal domain (sites III and IV) bind $Ca^{2+}$ with high affinity. At submicromolar concentrations of $Ca^{2+}$, the metal binding sites in the C-terminal domain of TnC are occupied with $Mg^{2+}$, whereas the $Ca^{2+}$-specific sites in the N-terminal domain are empty. In this case the N-terminal region of TnI is bound to the C-terminal domain of TnC, whereas the inhibitory C-terminal regions of the TnI molecule interact with actin and tropomyosin but not with TnC. When the $Ca^{2+}$-concentration increases up to micromolar level, $Ca^{2+}$ binds to the N-terminal, $Ca^{2+}$-specific low affinity sites of TnC. The $Ca^{2+}$-binding increases the affinity of this domain for the inhibitory and C-terminal regions of TnI, resulting in the release of those fragments from actin and tropomyosin and making strong contact with the extended central and N-terminal regions of TnC. This high-affinity binding of the components of the troponin complex results in important conformational changes of both molecules.

In human striated muscle, three forms of TnI were found: two for skeletal muscle (h.sk. TnI) and one for cardiac muscle (h.c. TnI). The three troponin forms have similar structures, but for human cardiac troponin I the existence of 33 extra amino acids in the N-terminal part of the molecule, as compared to the skeletal TnI isoform, was shown. This extra polypeptide and also some changes in the amino acids make it possible to differentiate human cardiac troponin I from the skeletal forms, for example by immunological methods. All existing diagnostic systems are based on immunological measurement of TnI in serum samples.

It has been shown that in the presence of micromolar and higher concentrations of $Ca^{2+}$, a mixture of troponins I and C exists in the form of a complex with strong interaction between both molecules. However, when the concentration of $Ca^{2+}$ in the solution decreases to submicromolar levels, $Ca^{2+}$ is washed away from the metal binding centers of TnC. After the $Ca^{2+}$ is removed, the interaction between the two proteins weakens and the conformation of TnI shows resemblance with the native (not complexed) protein.

The concentration of $Ca^{2+}$ in human serum is high enough for the two low-affinity centers of TnC to bind $Ca^{2+}$. It means that in the serum of patients with AMI or in patients with various skeletal muscle diseases, a major part of the TnI should be present in the form of a complex with TnC. Our experiments confirmed this hypothesis. We have shown in Katrukha et al. Clinical Chemistry 43:8 1379-1385 (1997), which is included herein as reference, that in the serum of AMI patients, the main part of TnI (50-90%) is presented in the form of a complex with TnC (and probably also with TnT). As mentioned above, the conformation of TnI in complex with TnC at high, i.e. micromolar or higher concentrations of $Ca^{2+}$ differs from the conformation of free TnI, or of TnI in complex with TnC at submicromolar concentrations of $Ca^{2+}$.

In common practice highly purified protein is used for the immunization of animals for the production of mono- or polyclonal antibodies. The conformation of purified TnI used for immunization and standard preparation is, however, different from that of TnI in complex with TnC. The change in conformation of the protein can decrease the affinity of the antibodies or make protein-antibody interaction impossible. In addition, due to the strong interaction between the two troponin molecules at micromolar and higher concentrations of $Ca^{2+}$, TnC will cover part of the surface of the TnI molecule and block some of the epitopes for some antibodies generated by the immunization of animals with highly purified troponin I. As a result, immunoassays based on the use of such antibodies, such as the main part of the commercially available antibodies developed for the said purpose, measure only the free TnI and a part of the TnI in complex with TnC in case the affinity constant of the antibodies is changed due to TnI-TnC interaction; or they measure only the free TnI is case the epitopes of the antibody are completely covered by TnC. In any case the concentration of TnI assayed by such systems in AMI serum samples will be different (lower) than the real concentration of this protein.

Thus there is a need for a method which would improve assays using such antibodies. Such a method would be useful not only in cases of diagnostic systems designed for assaying the cardiac form of TnI in serum but also in immunoassays developed for measurement of skeletal forms of TnI for diagnosis of skeletal muscle tissue necrosis.

In common practice, purified antigen is usually used for the preparation of calibrators or standard preparations for the immunoassays. In case of TnI, the purification is usually a complicated process that takes several days and includes several steps of column chromatography (affinity, ion exchange, etc.). It is a well known fact that TnI is highly susceptible to proteolysis. During long-term purification, the troponin I molecule can be partially cleaved by proteases and thus some part of the epitopes for some antibodies can be lost. In addition, all existing methods for TnI purification include stages in which highly concentrated (6-8M) urea solutions are used to dissociate the components of the troponin complex. Such rigid treatment can lead to irreversible changes in the conformation of some parts of the TnI molecule. Consequently the conformation of the TnI molecules in highly purified preparations can be different from that of the native protein. In addition, long-term contact of the protein with urea at high concentrations can result in a partial carbamylation of the TnI molecule. Thus the immunological activity of highly purified TnI can be different from that of native TnI.

SUMMARY OF THE INVENTION

The object of the invention is to provide an improved immunoassay diagnostic method for assaying troponin I in a sample from the blood stream of a patient, comprising determining the troponin I concentration in the sample using a standard, the standard comprising a complete native troponin complex.

In case the sample should be treated to dissociate the troponin components, the sample should be brought in contact with a $Ca^{2+}$-binding agent. The amount of $Ca^{2+}$-binding agent used is such as to be sufficient to decrease the $Ca^{2+}$-concentration in the sample to submicromolar level, thus decreasing the TnI-TnC interaction.

A further object of the invention is a kit for use in a method for improving the sensitivity of a diagnostic immunoassay method for assaying troponin I in a sample from the blood stream of a patient, the kit containing a mono- or polyclonal antibody to troponin I, a detectable label and a standard in the form of a complete native troponin complex. The kit can further contain a $Ca^{2+}$-binding agent.

A still further object of the invention is the use of a complete native troponin complex, isolated and purified from muscle tissue in mild conditions, for the preparation of a TnI-calibrator or standard. Such a standard preparation is used in the assay method and the kit according to the invention.

DETAILED DESCRIPTION OF THE INVENTION

The method according to the invention is carried out as an immunoassay method using mono- or polyclonal antibodies to TnI, that is antibodies either to human cardiac or skeletal troponin I depending on the specific troponin antigen to be assayed.

The immunoassay method can be any one of the known immunoassay methods suitable for the purpose, such as an enzyme immunoassay, radioimmunoassay, chemiluminescence immunoassay or fluoroimmunoassay method, etc. Such immunoassay systems are well known to a person skilled in the art and also commercially available.

According to one embodiment of the invention, the method is performed as a sandwich immunoassay method, using pairs of preferably monoclonal anti TnI antibodies, one antibody functioning as a "capture" antibody immobilized on a solid phase, and the second antibody carrying the label and functioning as the "detection" antibody.

According to the invention, such a diagnostic immunoassay method can be performed by bringing the sample to be assayed into contact with an agent or reactant capable of binding or complexing with $Ca^{2+}$. According to the invention, such a $Ca^{2+}$-binding agent can be any substance which, on the one hand, has an affinity constant to $Ca^{2+}$ sufficient to reduce the $Ca^{2+}$ level to submicromolar, and, on the other hand, does not negatively interfere with the assay method.

The $Ca^{2+}$-binding agent is preferably used in the form of a solution, preferably an aqueous solution, or a buffer solution, compatible with the assay.

A preferred group of $Ca^{2+}$-binding agents are the metal chelate forming agents which bind metals, including $Ca^{2+}$, in aqueous solutions. The group of metal chelate forming agents is well known to the person skilled in the art and includes such substances as polyoxycarboxylic acids, polyamines, ethylenediamine tetraacetic acid (EDTA), nitrilotriacetic acid (NTA) and ethyleneglycol-O,O'-bis(2-aminoethyl)-N,N,N',N'-tetraacetic acid (EGTA), and similar agents. Preferred substances are EDTA and EGTA in aqueous solution.

According to the invention, the $Ca^{2+}$-binding agent in the form of a solution is brought into contact with the sample to be assayed. This can take place by adding the $Ca^{2+}$-binding solution directly to the sample or, in a sandwich immunoassay method, to the buffer used in the assay during incubation with the blood sample.

The $Ca^{2+}$-binding agent is used in an amount sufficient to decrease the troponin I—troponin C interaction by binding enough $Ca^{2+}$ in order to reduce the level of $Ca^{2+}$ in the assay medium to submicromolar level. The decrease of interaction results in better exposure of TnI which then can be assayed.

The standard for use in the method of the invention comprises the complete native troponin complex, containing TnI, TnT and TnC in equimolar concentrations. The complex is isolated from muscle tissue, such as human cardiac tissue, in mild conditions, i.e. at low temperatures (+2 to +4° C.), and using as buffers dilute salt solutions with substantially neutral pH values.

The method described in Katrukha et al., "*Biochemistry and Molecular Biology International*" vol. 36, No. 1, 1995, p. 195-202 is too rigid for this purpose as it uses EDTA containing buffer solutions for the extraction of troponin, and for the washing of the affinity column. Thus decreasing interaction with the components of the complex part of TnC is lost during washing steps. Therefore TnI:TnC ratio in protein solution that is eluted from affinity column will be significantly higher than 1. Treatment of the TnI with low pH (e.g. pH 2) as well as urea can also affect the the conformation of the protein and it will be different from that in native complete troponin complex. That is why the proteins that are isolated by said Katrukha et al. method, is in fact not a "complete native troponin complex" which could be used as a standard preparation in the present invention.

We have in fact confirmed the idea that treatment of TnI with high urea concentrations affects the conformation of troponin and thus on the interaction of some antibodies with the antigen. In different sandwich immunoassays utilising monoclonal antibodies with different epitope specificities we tested native troponin complex and the same complex after short pre-treatment with urea containing buffer. As can be seen from FIG. 8, some pairs of antibodies recognise TnI in complex pre-treated with urea differently from that of non-treated. We consider this fact as a confirmation of our idea that the conformation of TnI is changed after urea treatment, and that troponin which was not treated with urea should be used for the preparation of standards and calibrations.

By using the complete complex, rather than purified TnI, one can thus avoid problems for example associated with changes in some epitopes on the troponin I which can take place for example during purification. We have also shown that the stability of TnI in the form of the native troponin complex is considerably higher compared to that of purified TnI, commonly used as a standard (see FIG. 6).

The present invention also contemplates a kit for use in an immunoassay method as defined above. Such a kit would include at least one mono- or polyclonal antibody to TnI, a detectable label, and a complete troponin complex as the standard. A $Ca^{2+}$-binding agent can also be included, preferably in the form of an aqueous solution. The label is attached to one of the immunoreactive components in order to provide a means for indicating the degree of immunological interaction and thus to allow for the determination of the TnI level in the sample. Consequently the label is of a type which can be detected by conventional methods for detection, such as using methods based on absorbance, luminescence, fluorescence or radioactivity. The detected signal can then be compared to standard curves. The standard curves are constructed by using in the standard preparation known amounts of the full troponin complex containing the three subunits described above, which has been derived directly from muscle tissue. Such a preparation has the advantage that it has better immunological properties than a preparation containing purified TnI. The troponin complex in the standard can be combined with a $Ca^{2+}$ binding agent, such as EDTA, added for example in a buffer, prior to measurement.

According to a preferred embodiment, the kit contains two monoclonal antibodies to TnI, to allow for a sandwich type of immunoassay. The first or capture antibody can in such a case be pre-attached to a solid phase, such as the wall of a micro-plate well. The second or detection antibody, which carries the label, can be provided in a suitable buffer solution. The optional $Ca^{2+}$-binding agent can be provided separately in an aqueous or buffer solution, or incorporated in the solution of the second antibody.

It is also possible to formulate the kit in the form of a well known immunochromatography strip. Such a strip can easily be used with whole blood, for example in order to diagnose AMI at an early stage, e.g. already in an ambulance in the case of emergency.

According to a preferred embodiment, we have used a two-step time resolved fluoroimmunoassay method, LANFIA, lanthanide fluoroimmunoassay. In this method a first biotinylated TnI antibody (capture antibody) is coated onto a solid phase, for example the surface of a streptavidin-coated micro plate well. After washing, the coated surface is then incubated in a second step with a mixture of the sample and a second labeled, e.g. Eu-chelate labeled antibody (detection antibody) in a buffer. A solution of the $Ca^{2+}$-binding agent can be added either to the sample or to the detection antibody solution. After washing and adding a LANFIA enhancement solution, the fluorescence signal (counts per second) is measured in a conventional manner. A description of the use of time-resolved fluorometry in immunoassay is to be found for example in "*Alternative Immunoassays*", ed. by Collins, W. P., John Wiley & Sons Ltd., 1985, Chapter 12.

DETAILED DESCRIPTION OF THE DRAWINGS

In the drawings,

FIG. 1 shows the troponin I epitope map. Five antigenic domains can be discerned for eight antitroponin I monoclonal antibodies, tested in our experiments. Three monoclonal antibodies (7F4, 11D7 and ES23) have unique epitopes; 8E10 and 5F1 have one and the same epitope; the epitopes of 10F4 and 10B11; and 8E10, 5F1 and 2A3 are overlapping.

Figure 2:
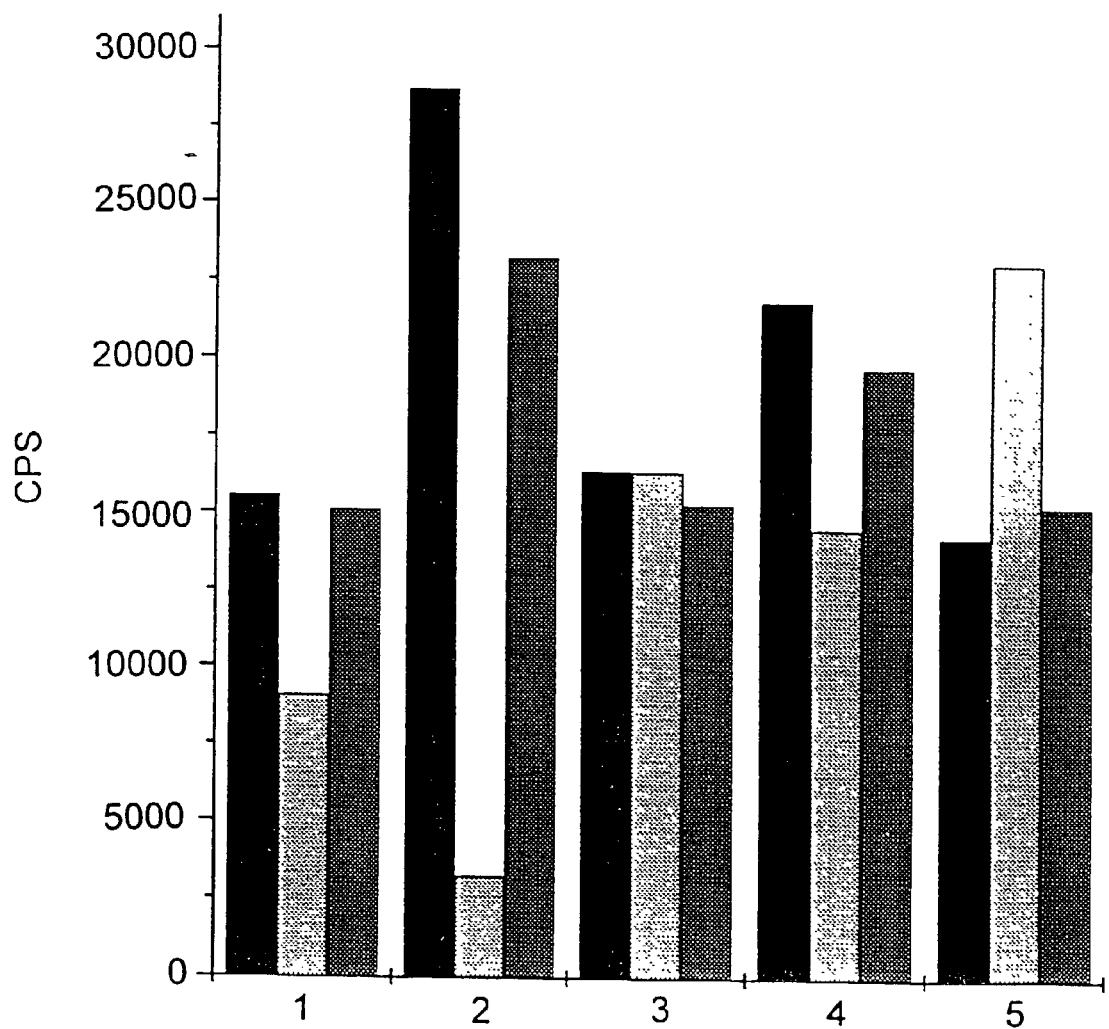

FIG. 2 shows the effect of troponin C on the immunological activity of troponin I for several pairs of antibodies (1-5 respectively):

| N | Biotinylated Ab | Eu-labeled Ab |
|---|---|---|
| 1 | 10F4 | 8E10 |
| 2 | 7F4 | ES23 |
| 3 | 7F4 | 2A3 |
| 4 | 10B11 | 2A3 |
| 5 | 7F4 | 10B11 |

The left hand column (black) shows the signal obtained while assaying a troponin I solution (30 ng/ml TnI in normal human serum), the middle column (light gray) the effect of adding five molar excess of troponin C, and the right hand column (dark grey) the effect of EDTA as a $Ca^{2+}$-binding reagent, added to the incubation mixture of TnI and TnC. Almost all assays (except #3) are effected to a different degree by adding TnC to a troponin I standard preparation. EDTA, added to an incubation mixture, restores the immunological activity of troponin I. Only for one antibody, ES23, the epitope remains partially covered (changed) by troponin C even in the presence of EDTA.

Figure 3A:
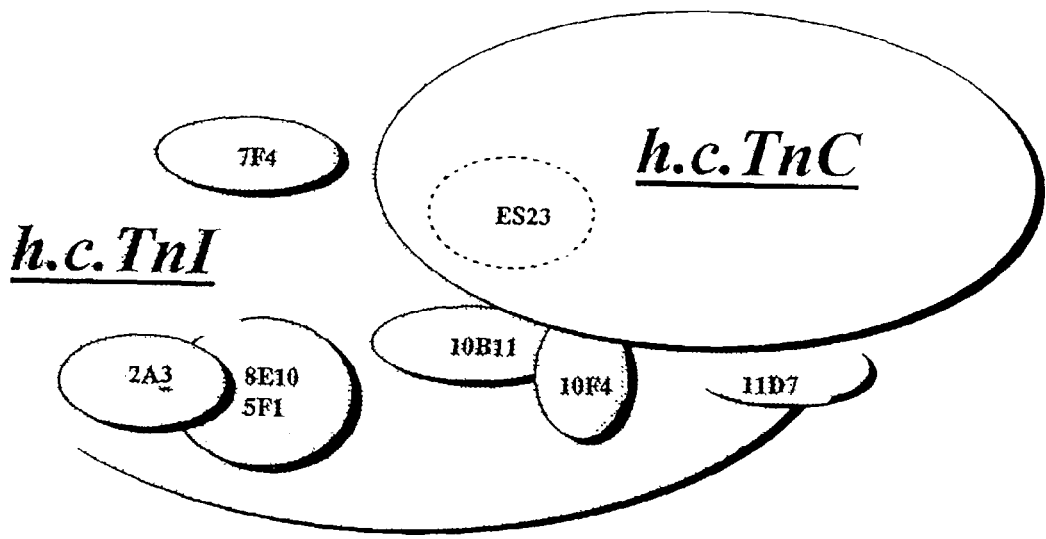
Figure 3B:
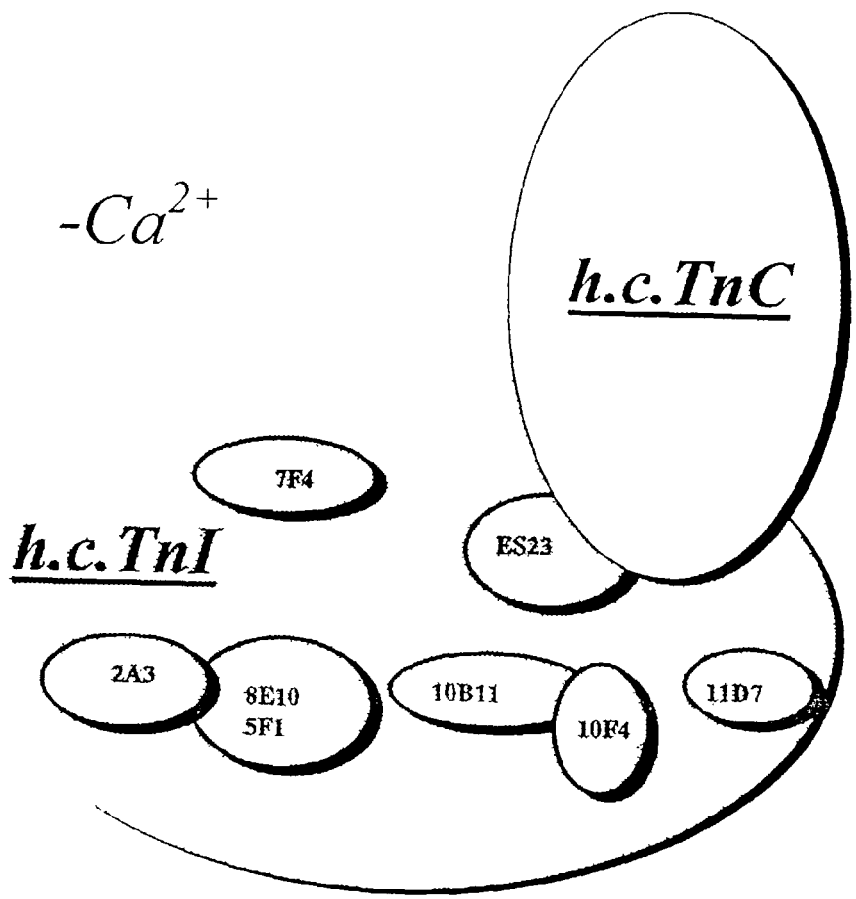

FIGS. 3A and 3B show the epitope map for tested antibodies in the presence of troponin C. The epitopes of 10B-11, 10F4, 11D7 and ES23 antibodies are changed or covered with troponin C in the presence of $Ca^{2+}$ (FIG. 3A). In case the concentration of $Ca^{2+}$ is decreased to a submicromolar level (—$Ca^{2+}$), the epitopes of all antibodies (except the epitope of ES23 antibody) are not covered or changed any more (FIG. 3B).

Figure 4A:
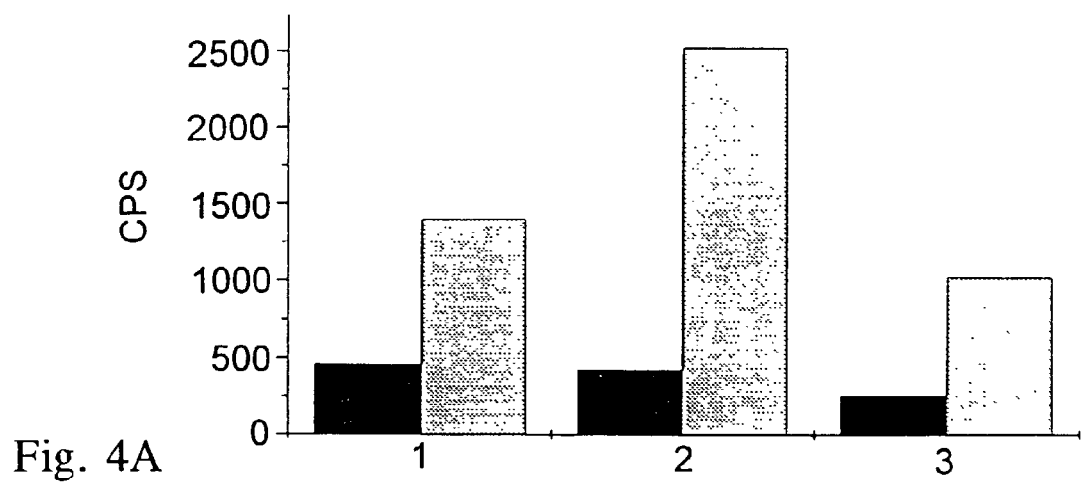
Figure 4B:
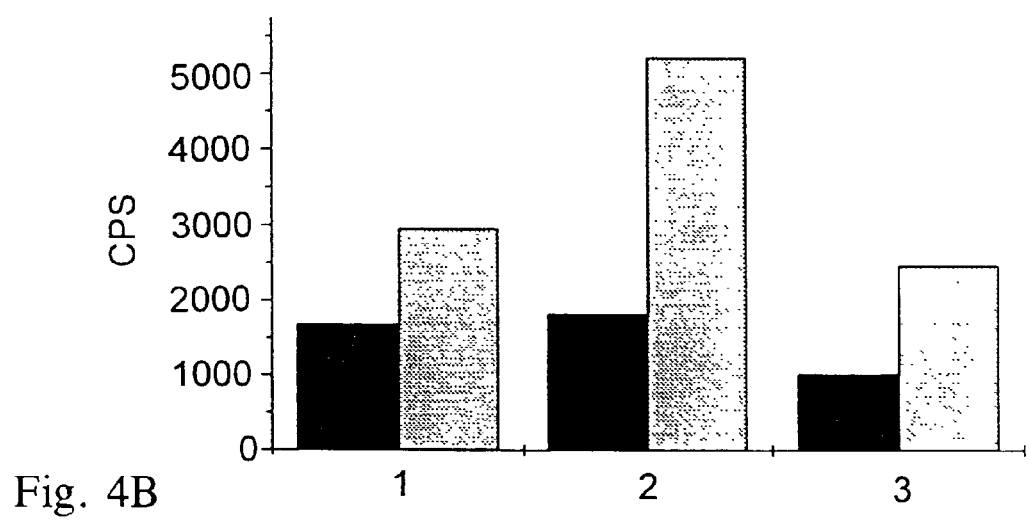
Figure 4C:
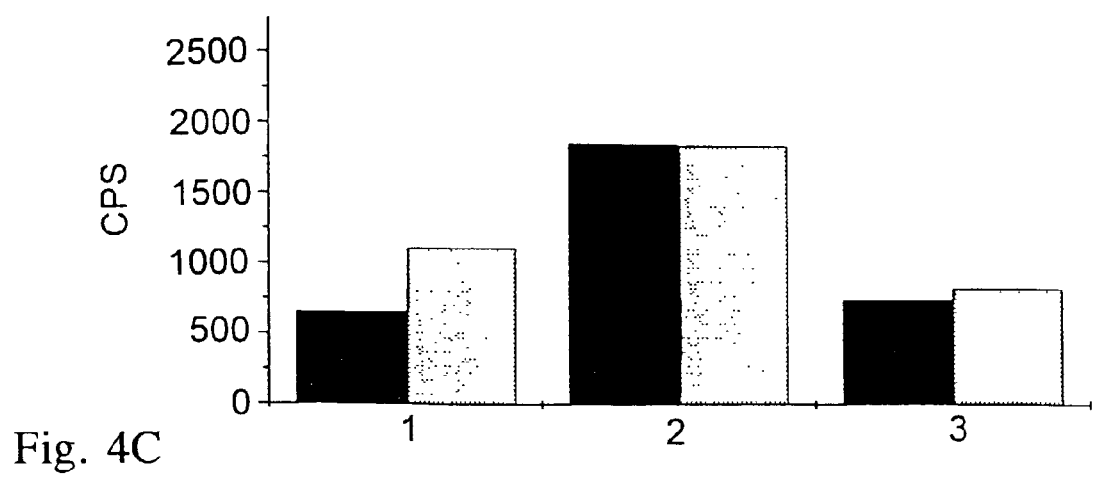

FIGS. 4A, 4B and 4C show the results of testing three serum samples (1, 2, 3) from AMI patients in three different assay systems (A, B, C).

| N | Biotinylated Ab | Eu-labeled Ab |
|---|---|---|
| A | 7F4 | ES23 |
| B | 10F4 | 8E10 |
| C | 2A3 | 10B11 |

The left hand column gives the signal from a serum sample without $Ca^{2+}$-binding agent, and the right hand column a similar sample but with added EDTA. The increase in the signal level after the addition of $Ca^{2+}$-binding agent to the sample is evident for the first two systems and is less evident in the case of the last system, suggesting that the epitopes of 2A3 and 10B11 antibodies are not strongly changed by troponin I—troponin C interaction.

Figure 5:
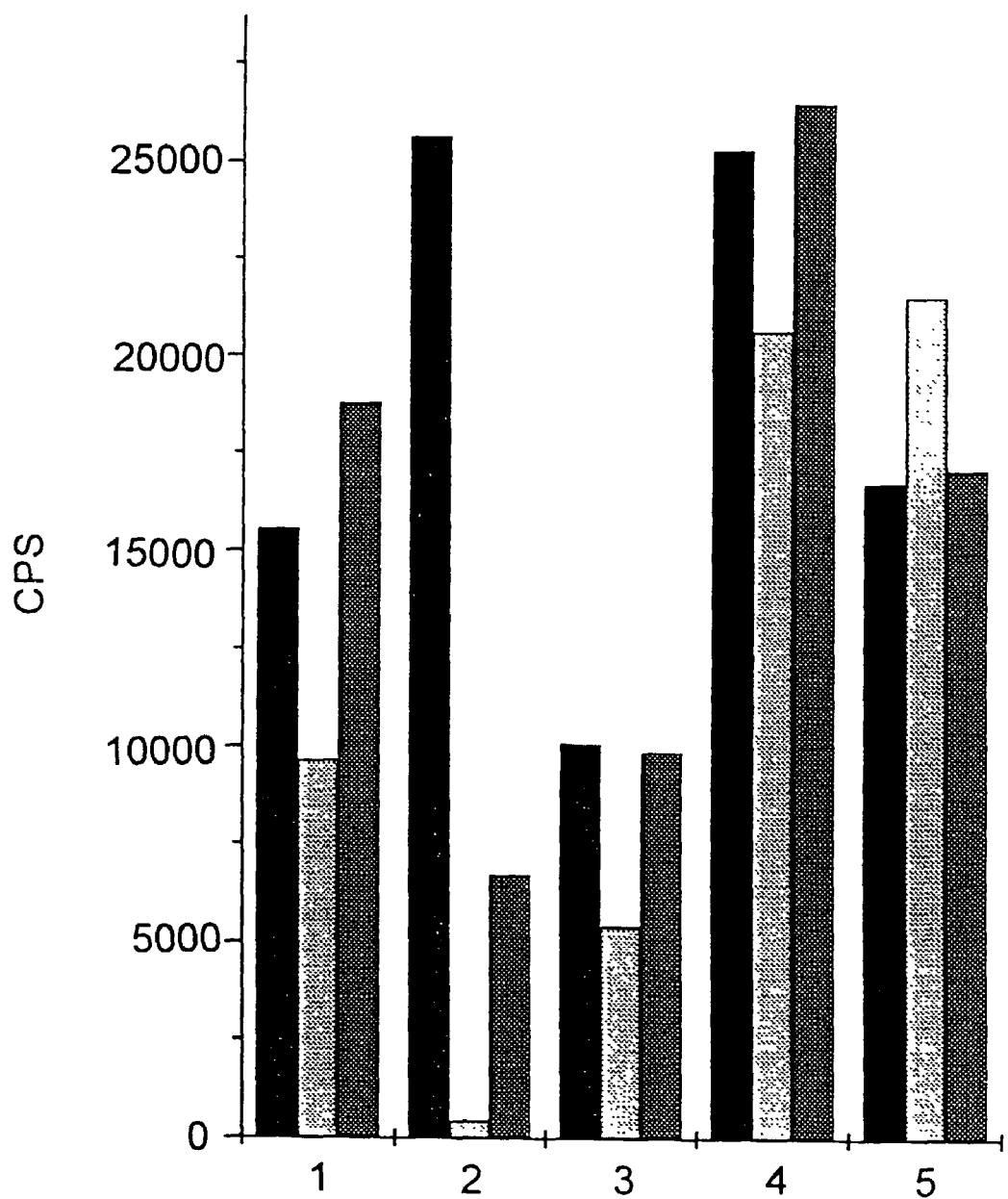

FIG. 5 shows the comparison of immunological activities of highly purified troponin I, dissolved in normal human serum in a concentration of 30 ng/ml and troponin I in the form of the native complex (purified in mild conditions) in the same concentration.

| N | Biotinylated Ab | Eu-labeled Ab |
|---|---|---|
| 1 | 10F4 | 8E10 |
| 2 | 7F4 | ES23 |
| 3 | 10F4 | 10B11 |
| 4 | 8E10 | 7F4 |
| 5 | 7F4 | 10B11 |

The black column shows the signal, obtained while assaying a troponin I solution, the light gray column shows the signal level when troponin complex in the presence of $Ca^{2+}$ was assayed, and the third column (dark grey) indicates the signal received when troponin complex in the presence of EDTA was assayed. For three tested pairs (#3,4,5) troponin I in the form of the native troponin complex in the presence of EDTA has the same immunological activity as the highly purified troponin I. For 10F4-biot-8E10-Eu antibodies, troponin I in complexed form has better activity than the purified troponin I. This fact confirms that during long term purification some epitopes of troponin I can change. From this point of view it is better to use troponin I in the form of the native complex for troponin I standard preparation. Only for one, ES23 antibody, the epitope remains partially covered (changed) by troponin C even in the presence of EDTA, as was the case when troponin C was added to troponin I solution.

Figure 6A:
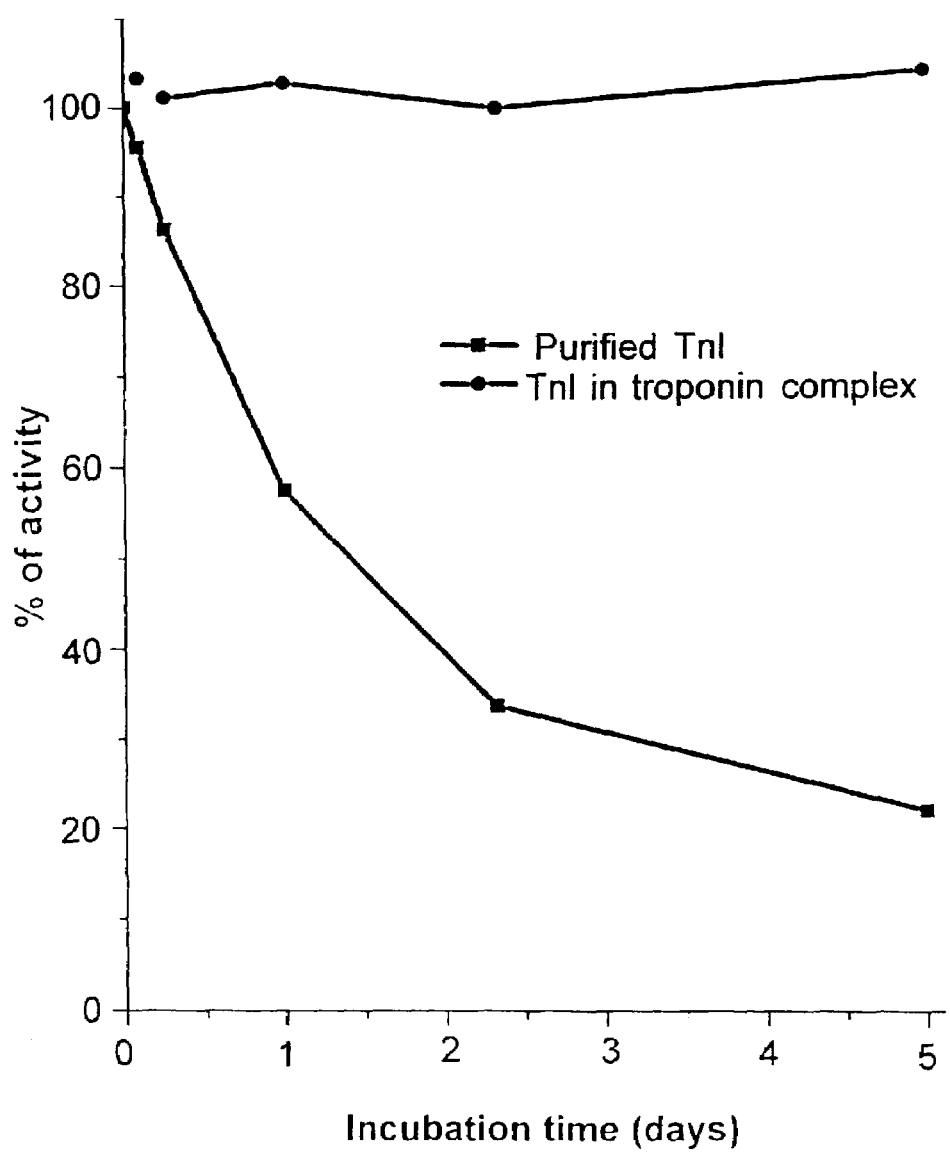
Figure 6B:
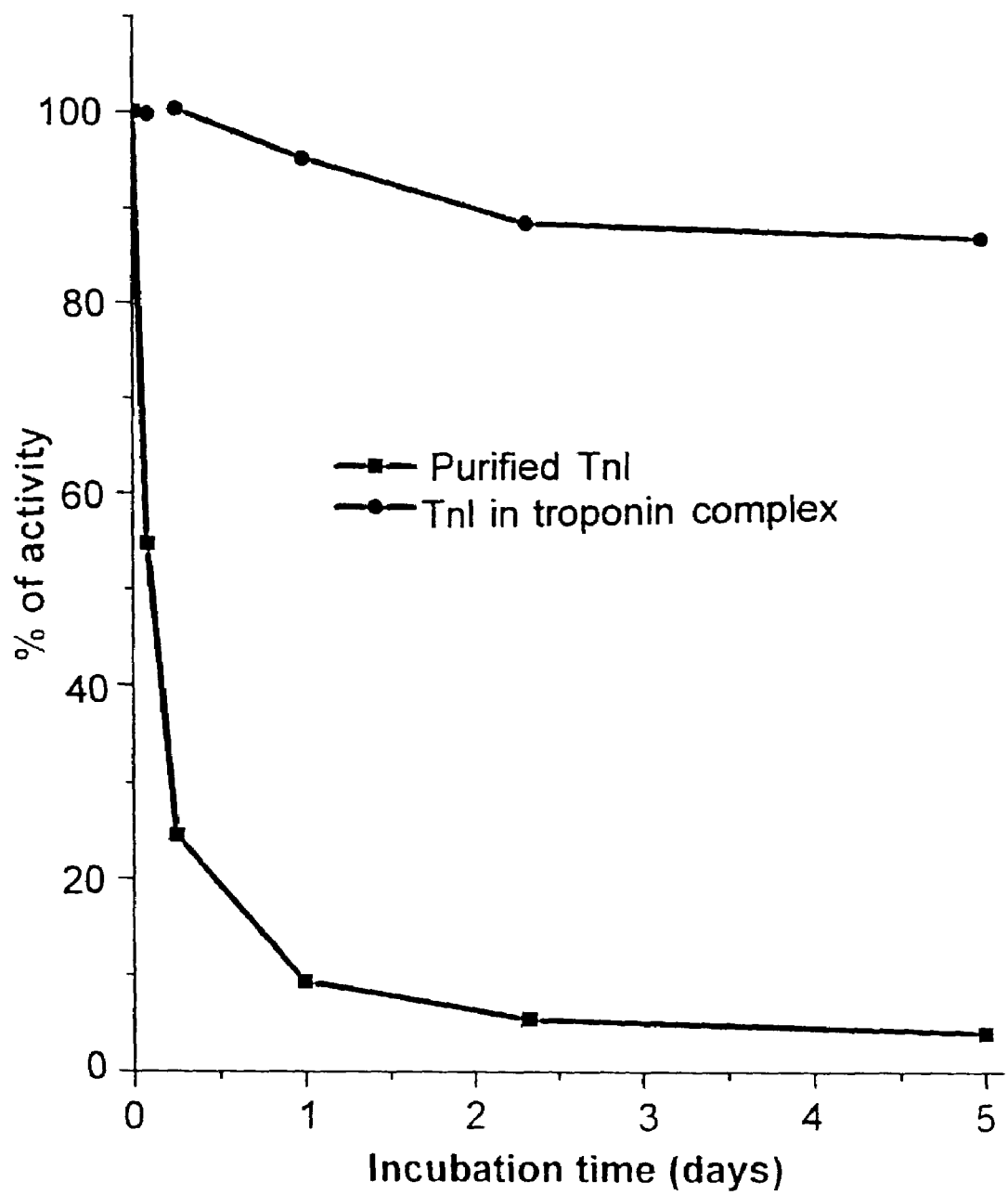

FIGS. 6A and 6B show the stability of purified TnI and TnI in the troponin complex incubated for one week at 4 and 20° C., respectively. The tests were carried out using human cardiac troponin complex (HyTest, Turku) in a 10F4-Biot-7F4-Eu assay. The complex was purified in mild conditions as described in the examples hereinafter, and contains all the components in equimolar proportions. The signal obtained in the assay with TnI in the form of the complex was higher than the signal obtained in assay with purified TnI. It confirms that during purification of TnI, the protein can change the native conformation. FIGS. 6A and 6B indicate that the stability of TnI in the native troponin complex is significantly higher than the stability of purified TnI protein.

Figure 7:
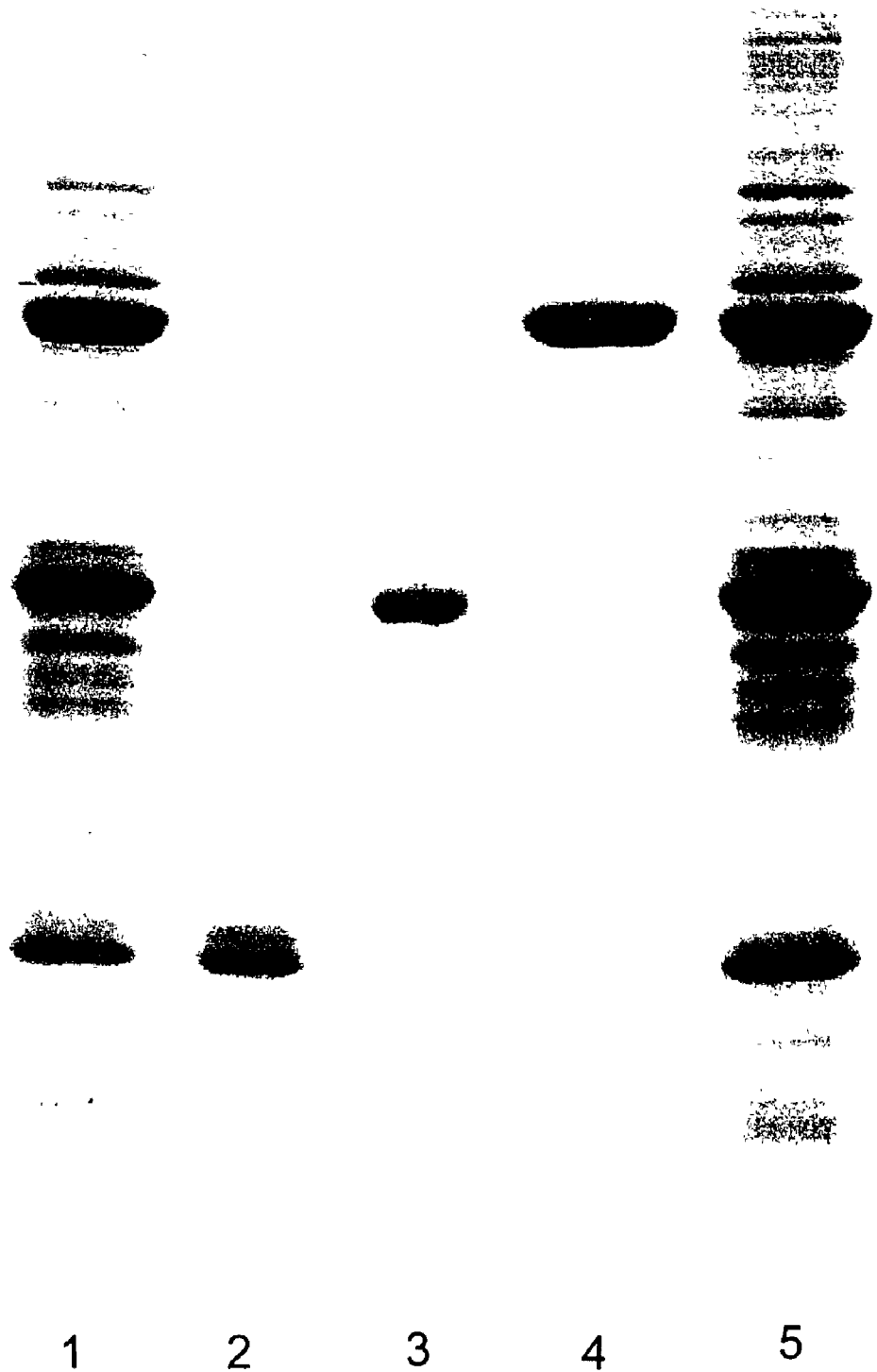

FIG. 7 shows SDS gel electrophoresis of native human cardiac troponin complex purified in mild conditions. From left to right: lanes 1 and 5: human cardiac troponin complex; lane 2: human TnC, lane 3: human cardiac TnI; lane 4: human cardiac TnT.

Figure 8:
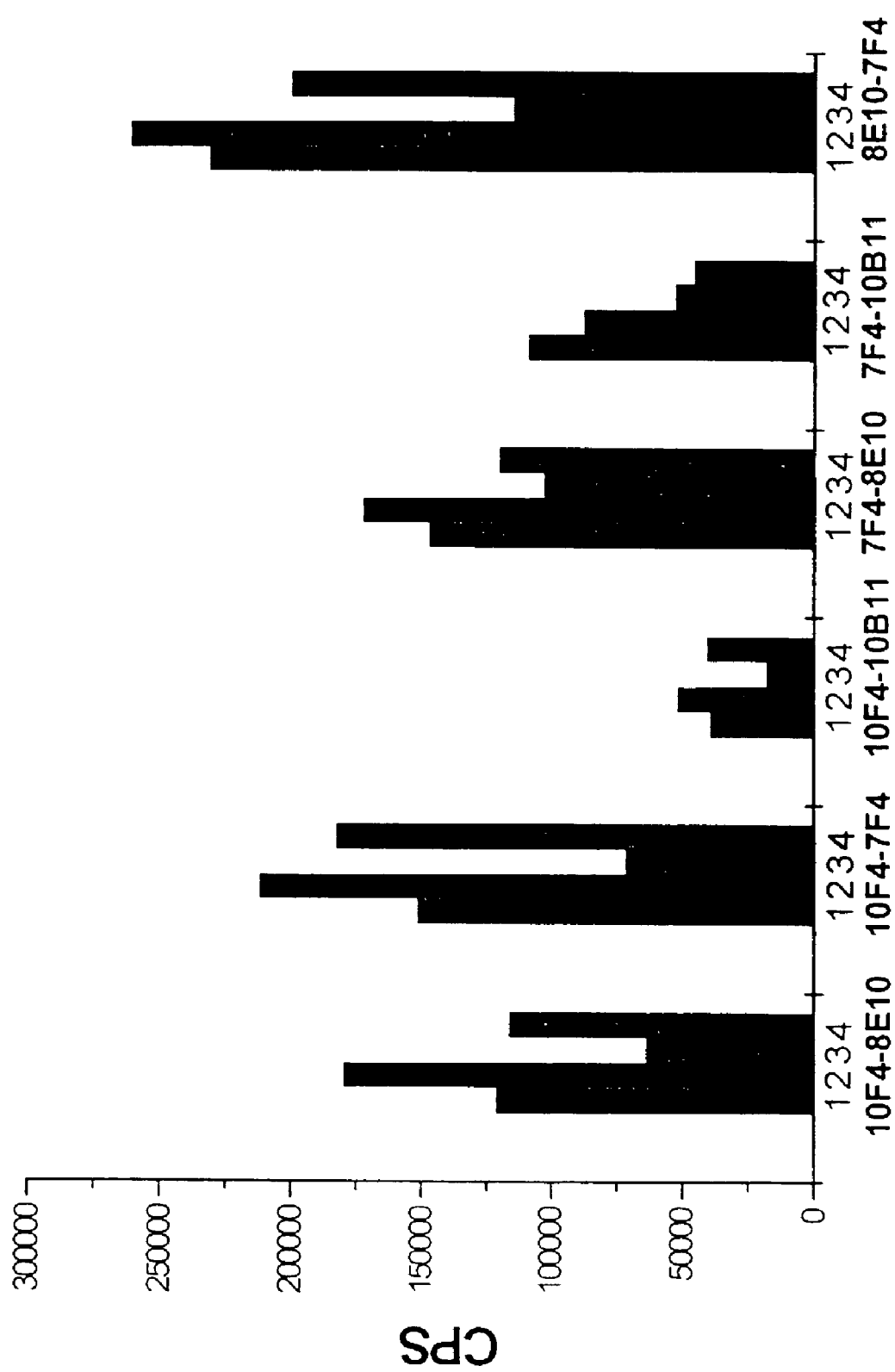

FIG. 8 shows the effect of urea treatment on the immunological activity of cTnI. In each experiment Column 1. is for TnI (30 ng/ml) in native complex without EDTA; Column 2. is for TnI (30 ng/ml) in native complex with 2 mM EDTA; Column 3. is for TnI (30 ng/ml) in complex treated with urea buffer without EDTA; and Column 4. is for TnI (30 ng/ml) in complex treated with urea buffer with 2 mM EDTA.

For all tested pairs of MAbs 10-30% decrease of the signal in case of urea treatment was observed. This experiment confirms suggestion that long-term contact of the protein with urea can result in partial changes of cTnI molecule conformation and thus affect on the antigen-antibody interaction.

EXAMPLES

Preparation of Complete Native Troponin Complex

All buffers used are dilute salt solutions having substantially neutral pH values. All purification steps should be performed on snow or in cold room. During all centrifugations the temperature inside the rotor should be kept at +2 to +4° C.

Homogenization of Human Cardiac Tissue and Extraction of Soluble Proteins.

100 g of cardiac muscle (w/o fat tissue) are thawed and homogenized in 0.5 l of Buffer 1 (Tris-HCl buffer, pH range from 7.5 to 8.5, containing $CaCl_2$ and protease inhibitors) in Waring Blendor for one minute (3 times) with 30 second intervals. One liter of Buffer 1 is added to the tissue suspension and it is centrifuged at 4500 g for 5 minutes.

Washing Procedure

After centrifugation the precipitate obtained is resuspended in 1.5 l of Buffer 2 (Tris-HCl buffer, pH range from 7.5 to 8.5, containing $CaCl_2$, protease inhibitors, detergent in the concentration of 0.01 to 1% and salts in the concentration of from 0.01 to 0.15 M), and centrifuged at 4500 g for 5 minutes.

The precipitate obtained is resuspended in 1.5 l of Buffer 3 (potassium-phosphate buffer, pH-range from 5.5 to 7.0) containing salts in the concentration of from 0.1 to 1 M, and protease inhibitors), and incubated with shaking for 30 min in cold room. After incubation it is centrifuged at 4500 g for 5 minutes.

The precipitate obtained is resuspended in 1 l of Buffer 4 (salt solution with concentration of salts from 0.1 to 10 mM, containing protease inhibitors), and centrifuged at 4500 g for 5 minutes.

The following procedure is repeated for four times: The precipitate obtained is resuspended in 1 l of Buffer 5 (salt solution with concentration of salts from 0.1 to 0.3 M, containing protease inhibitors), and centrifuged at 4500 g for 5 minutes.

The following procedure is repeated for four times: The precipitate obtained from the previous step is resuspended in 1 l of Buffer 4 and centrifuged at 4500 g for 5 minutes.

Complex Extraction

The precipitate obtained is suspended in 0.5 l of Buffer 6 (salt solution with concentration of salts from 0.1 to 0.5 M, containing protease inhibitors), and incubated for two hours in cold room with gentle shaking, and then centrifuged for one hour at 10 000 g.

Complex Precipitation and Purification

The supernatant obtained from the extraction step is precipitated with ammonium sulfate, and the precipitate is dialysed for 15 to 20 hours in Buffer 7 (Tris-HCl buffer, pH range from 7.5 to 8.5, containing salts in the concentration of from 100 to 300 mM, and protease inhibitors). The aliquots of the complex obtained are stored in plastic tubes at −70° C. The complex obtained contained cTnI, cTnT and cTnC in equimolar concentrations, and was of 80 to 85% of purity (see FIG. 7).

Urea Treatment of the Troponin Complex

Concentrated preparation of the troponin complex (3 mg/ml) was reconstituted in 9 volumes of urea containing buffer (7 M urea, 10 mM mercaptoethanol, 5 mM EDTA and 20 mM Tris-HCl, pH 7.5), incubated for 30 min on ice and then reconstituted in normal human serum up to the concentration 30 ng/ml. Buffers with high urea concentrations are commonly used to separate the components of troponin complex on several steps of cTnI purification. Control sample was prepared in the same way, but without urea treatment. The influence of 7 M urea treatment on immunological activity of cTnI in the form of native troponin complex was studied in sandwich fluoroimmunoassay utilising five different combinations of anti-cTnI MAbs. The results are seen in FIG. 8.

Preparation of Whole Troponin Complex for Troponin I Purification

The troponin I that we used for mouse immunization, hybridoma testing and for TnI standard preparation was prepared using a method described in "*Biochemistry and Molecular Biology International*", vol. 36, No 1, 1995, p.195-202 or a method slightly modified thereof.

10 grams of muscle tissue were homogenized at top speed in 100 ml of buffer 1 containing 20 mM Tris/HCl, pH 7.5, 0.1 mM phenylmethylsulfonyl fluoride (PMSF), 5 mM $CaCl_2$.

The homogenate was centrifuged for 10 min. at 10,000 g and the pellet was homogenated for a second time in the same volume of the same buffer, containing 1% of Triton X-100. After centrifugation the pellet was homogenated in 100 ml of 150 mM potassium phosphate buffer (buffer 2) pH 6.5, containing 0.3 M KCl, 0.2 mM ATP, 1 mM PMSF. After centrifugation for 30 min. at 10000 g the pellet was suspended in 100 ml of cold 25 mM Tris/HCl buffer, pH 7.5 containing 0.7 M LiCl, 5 mM $CaCl_2$, PMSF (buffer 3). The suspension was stirred for 30 min. at 0° C. and then centrifuged for 1 hour at 10000 g. The supernatant was filtrated through paper filters and then loaded on an affinity column containing immobilized anti-troponin I monoclonal antibody (clone C5, antibodies of this clone crossreact with the skeletal and cardiac forms of troponin I wherefore this column can be used for the preparation of skeletal and cardiac forms of troponin). The affinity column was pre-equilibrated with buffer 3. The column was washed with several volumes of buffer 3 and troponin was eluted with 0.1 M glycine buffer pH 2.0, containing 5 mM $CaCl_2$. Then the protein was dialyzed against buffer 3 overnight. The yield is usually 12-15 mg of troponin from 10 g of muscle tissue. According to the SDS-gel electrophoresis, the troponin was sligthly contaminated by unidentified proteins. The concentration of troponin I and troponin T was determined by scanning gels with troponin complex and troponin I and troponin T standard preparations.

Monoclonal Antibody Preparation

BALB/c mice were immunized with purified troponin I using a standard protocol: Briefly, mice were injected intraperitoneally on day 1 with 100 μg of human cardiac troponin I in complete Freund's adjuvant. On days 31 and 61, the mice were boosted intraperitoneally with 100 μg of troponin I in incomplete Freund's adjuvant. The final boosts were administered on days 91 and 93 with 50 μg of the antigen in phosphate-buffered saline, pH 7.4, injected both intraperitoneally and intravenously. On day 96, the mice were killed, their spleens were removed, and splenocytes were isolated for fusion. Splenocytes were fused to a nonsecretor cell line sp2/0 and plated into Dulbecco's Modified Eagle's Medium containing hypoxanth, aminopterin, and thymidine (HAT) with 15% of fetal bovine serum.

Wells exhibiting hybridoma growth in HAT medium were screened for the production of anti-troponin I antibodies. For this purpose, hybridoma culture media were incubated for 30 minutes at 37° C. in micro-ELISA plates coated with troponin I (300 ng/well) and after washing incubated with HRP-labeled goat anti-mouse IgG antibodies. After washing, HRP activity was determined by using o-phenylenediamine/hydrogen peroxide as a substrate and 1 M sulfuric acid as a stop reagent and 30 minutes for color development. Positive hybridomas were retested for antibody specificity by using micro-ELISA wells coated with the skeletal form of troponin I.

Hybridomas selected on the basis of specificity were cloned by two rounds of limiting dilution into aminopterin-free (HT) medium. Stable hybridoma clones were cultured as ascite tumors in BALB/c mice. Monoclonal antibody specificity was checked once more using h.c.TnI and h.sk. TnI coated micro-ELISA plates and different dilution of ascites fluid.

Monoclonal antibodies were purified from ascites fluids with Protein A-Sepharose affinity chromatography (Pharmacia). Antibody concentrations were determined by Lowry method using mouse IgG (Calbiochem) as a standard.

The specificity of monoclonal antibodies was confirmed by Western blotting. Purified monoclonal antibodies were incubated (3 μg/ml, 1 hour, 37° C.) with Western blot membranes, containing purified proteins—h.c.TnI and h.sk. TnI transferred from a SDS-PAGE gel (7.5-15% gradient gel). After washing and one hour of incubation with HRP-labeled goat anti-mouse antibodies at 37° C., protein bands were made visible after incubation with 4-chloro-1-naphthol/hydrogen peroxide substrate. All antibodies described here were h.c.TnI specific without crossreaction with h.sk. TnI.

Antibody Biotinylation

For antibody biotinylation we have used biotinamidocaproate N-hydroxysuccinimide ester. Briefly the biotinylation reagent was dissolved in dimethyl sulfoxide in a concentration of 10 mg/ml. The antibody solution (3 mg/ml) was prepared in 0.1 M borate buffer pH 8.8. The biotinylation reagent was added to the antibody solution at a ratio 200 μg of ester per milligram of antibody, mixed well and incubated at room temperature for 4 hours. Then 17 μl of 1M $NH_4Cl$ per 200 μg of biotin ester were added and after 10 min. of incubation at room temperature, the buffer was changed using NAP™-5 and NAP™-10 columns (Pharmacia, Uppsala, Sweden) preequilibrated with 50 mM Tris/HCl buffer pH 7.75 containing 0.9% of NaCl and 0.05% of $NaN_3$.

Antibody Eu-Labeling

Stable fluorescent chelates of EU used to label the detection antibodies were obtained from Wallac Oy (Turku, Finland). We used an Eu chelate of 4-[2-(4-isothiocyanatophenyl)ethynyl]-2,6-bis{[N,N-bis(carboxymethyl)-amino]methyl}pyridine. Labeling of monoclonal antibodies with the Eu-chelate was performed overnight at +4° C. with a 200-fold molar excess of the chelate in 50 mM sodium carbonate buffer, pH 9.8 The labeled antibodies were separated from the excess of free chelate by gelfiltration on a Superdex™ 200 HR 10/30 column (Pharmacia, Uppsala, Sweden) The column was preequilibrated with 50 mM Tris/HCl buffer pH 7.75 containing 0.9% of NaCl and 0.05% of $NaN_3$. The labeling degree of the pooled antibody fraction was determined against an Eu-calibrator.

Pre-incubation of Streptavidin-coated Plates with Biotinylated Anti-TnI Antibodies Biotinylated antibodies were incubated in the wells of a streptavidin-coated micro-well plate for 30 mins at room temperature using a concentration of 400 ng of antibody per well in 0.2 ml of DELFIA® buffer, with gentle shaking. DELFIA assay buffer contains, per liter, 50 mM Tris/HCl, pH 7.75, 9 g of NaCl, 5 g of BSA, 0.5 g of bovine serum γ-globulin, 0.1 g of Tween® 40, 20 μM DTPA, 0.5 g of $NaN_3$ and 20 mg of cherry red.

After incubation, the plates were washed two times with DELFIA® washing solution.

Incubation of Labeled Antibodies with Serum Samples in the Pre-absorbed Plates

In the second step, AMI serum samples were incubated with Eu-labeled antibodies (200 ng/well) and with EDTA in 5 mM concentration for 30 min at room temperature while gently shaking. 0.025 ml of serum and 0.1 ml of antibody solution in Delfia buffer per well was used. The EDTA-solution can be added either directly to the serum sample or to the labeled antibody solution.

After incubation, the plate was washed 6 times with DELFIA® washing solution and thereafter 0.2 ml of LAN-FIA enhancement solution per well was added. After incubation for 3 min with gently shaking, the signal was measured.

Instead of using a EDTA as solution in water, a solution in DELFIA® buffer (pH adjusted to 7.7-7.8) can be used. In place of EDTA, EGTA (ethyleneglycol-O,O'-bis(2-aminoethyl)-N,N,N',N'-tetraacetic acid) in solution with water or buffer can be used in the same concentration as EDTA.

The above system was also used for obtaining the results shown in the FIGS. 2, 4 and 5, by using instead of the serum sample, troponin I solution in normal human serum with or without troponin C, made for example according to the method of Katrukha et al., "*Biochemistry and Molecular Biology International*" vol. 36, No 1, 1995, p. 195-202.

Epitope Mapping

In our experiments we have used eight monoclonal antibodies specific to the cardiac form of human troponin I without crossreaction with skeletal forms of troponin I. All possible combinations of those antibodies for sandwich fluoro immunoassay were tested. The first monoclonal antibody was biotinylated and immobilized on microtiter strip wells, the second one was labelled with europium chelate as is described above. All combinations were tested for reactivity with highly purified human cardiac troponin I. The FIG. 1 shows the troponin I epitope chart based on the checked board experiments and determination of crossreactivities.

Troponin C while binding to troponin I in the presence of $Ca^{2+}$ covers part of the troponin I surface, thus changing the epitopes of some anti-troponin I antibodies, developed after immunization of the animal by purified troponin I. We have checked in sandwich immunoassay the interaction of different pairs of antibodies with purified troponin I and with troponin I in the presence of 5 molar excess of troponin C (with and without $Ca^{2+}$). FIG. 2 shows that for some pairs of antibodies the addition of troponin C to troponin I standard decreases the signal level. Addition of 5 mM EDTA restores the immunological activity of troponin I by decreasing troponin I—troponin C interaction.

The invention claimed is:

1. A troponin I standard or calibrator preparation comprising a complete native vertebrate troponin complex comprising an equimolar proportion of troponin I, troponin T and troponin C, said complex prepared by the process of isolating said complete native troponin complex from vertebrate cardiac or skeletal muscle tissue under mild conditions comprising a temperature of from about 2° C. to about 4° C. and using as a buffer a dilute salt solution with neutral pH values.

2. The preparation according to claim 1, wherein the preparation is in a medium comprising normal human serum.

3. A method for preparing a troponin I standard or calibrator, comprising
isolating and purifying a complete native troponin complex comprising an equimolar proportion of troponin I, troponin T and troponin C, under mild conditions comprising a temperature of from about 2° C. to about 4° C. and using as a buffer a dilute salt solution with neutral pH values from vertebrate cardiac or skeletal muscle tissue, and
adding the complex obtained to normal human serum.

4. An iminunoassay kit for diagnostic assaying of troponin I in a serum sample of a patient, the kit comprising:
a monoclonal antibody or polyclonal antibody to troponin I,
a detectable label, and
a standard or calibrator preparation according to claim 1.

5. The kit according to claim 4, further comprising a $Ca^{2+}$-binding agent.

6. The kit according to claim 4, wherein the detectable label is a fluorescent label.

7. An immunoassay kit for diagnostic assaying of troponin I in a serum sample of a patient, the kit comprising
(a) a first monoclonal capture antibody to human cardiac troponin I,
(b) a second monoclonal detection antibody to human cardiac troponin I, wherein the second antibody is fluorescently labeled, and
(c) a standard or calibrator preparation according to claim 1.

8. The kit according to claim 7, wherein said first monoclonal antibody is immobilized onto a solid phase.

9. A diagnostic immunoassay method for assaying troponin I (TnI) in a serum sample of a patient, comprising
(a) determining the troponin I content of the sample;
(b) preparing a standard curve using a troponin I standard of calibrator preparation comprising a complete native vertebrate troponin complex comprising an equimolar proportion of troponin I, troponin T and troponin prepared according to claim 1,
(c) comparing the value of the troponin I content obtained in step (a) to the standard curve produced in step (b).

10. The method according to claim 9, wherein the immunoassay method is a fluoroimmunoassay method.

11. The method according to claim 9, wherein the immunoassay method is a sandwich immunoassay, using a first capture anti TnI antibody and a second detection anti TnI antibody.

12. The method according to claim 9, wherein the troponin I is human cardiac troponin I.

* * * * *

UNITED STATES PATENT AND TRADEMARK OFFICE
CERTIFICATE OF CORRECTION

PATENT NO. : 7,285,418 B2 Page 1 of 1
APPLICATION NO. : 10/187310
DATED : October 23, 2007
INVENTOR(S) : Alexei G. Katrukha et al.

It is certified that error appears in the above-identified patent and that said Letters Patent is hereby corrected as shown below:

Title Page:

Item (74), "Marshall" should be -- Marshall, --.

In the Claims:

At Column 12, line 21, "neutral pH values" should be -- a neutral pH value --.

At Column 12, lines 48-50, "using a troponin I standard of calibrator preparation comprising a complete native vertebrate troponin" should be -- using as a standard a purified preparation of a complete native troponin --.

At Column 12, lines 51-52, "and troponin prepared according to claim 1," should be -- and troponin C; and, --.

At Column 12, lines 55-56, "immunoassay" should be -- diagnostic --.

At Column 12, lines 57-58, "immunoassay" should be -- diagnostic --.

Signed and Sealed this

Seventeenth Day of June, 2008

JON W. DUDAS
*Director of the United States Patent and Trademark Office*